United States Patent [19]
Bachalo

[11] Patent Number: 4,986,659
[45] Date of Patent: Jan. 22, 1991

[54] METHOD FOR MEASURING THE SIZE AND VELOCITY OF SPHERICAL PARTICLES USING THE PHASE AND INTENSITY OF SCATTERED LIGHT

[75] Inventor: William D. Bachalo, Los Altos Hills, Calif.

[73] Assignee: Aerometrics, Inc., Sunnyvale, Calif.

[21] Appl. No.: 416,519

[22] Filed: Oct. 3, 1989

Related U.S. Application Data

[63] Continuation-in-part of Ser. No. 162,053, Feb. 29, 1988, abandoned.

[51] Int. Cl.⁵ ............................................. G01N 15/02
[52] U.S. Cl. ..................................... 356/336; 356/343
[58] Field of Search ...................... 356/336, 338, 343

[56] References Cited

U.S. PATENT DOCUMENTS

| | | | |
|---|---|---|---|
| 4,179,218 | 12/1979 | Erdmann et al. | 356/336 |
| 4,329,054 | 5/1982 | Bachalo | 356/336 |
| 4,537,507 | 8/1985 | Hess | 356/336 |
| 4,540,283 | 9/1985 | Bachalo | 356/336 |
| 4,701,051 | 10/1987 | Buchhave et al. | 356/336 |

*Primary Examiner*—Richard A. Rosenberger
*Attorney, Agent, or Firm*—Blakely, Sokoloff, Taylor & Zafman

[57] ABSTRACT

An improved apparatus and method for determining the change in the effective cross-section of a sample volume defined by two crossed laser beams is disclosed. A laser generation means is provided for generating a pair of coherent laser beams and means are provided to change the separation, intersection angle, and focused diameter of the beams. These beams are directed along an axis, and are caused to cross the axis at a given angle to define an interference pattern constituting a sample volume. A collection apparatus for sensing the scattering of light caused by particles, droplets, bubbles, or the like within the sample volume is provided. In the presently preferred embodiment, the collection apparatus is disposed at preferred off-axis angles including off-axis backscatter with the angle predetermined, and the angle defined by the direction of beam propagation. The collected scattered light is directed onto photo-detectors which are coupled to a signal phase determining means, for measuring the relative phase between the signals produced by each photo-detector and a signal amplitude determining means to measure the relative amplitude of the signals produced as the particle, drop, bubble, or the like passes through the sample volume. Sizing means are coupled to the signal phase and amplitude determination means for determining the size of the particle, drop, bubble, or the like from phase and amplitude changes in the received signals. Methods and apparatus are disclosed for determining the change in the effective cross-section of the sample volume due to size variations of particles passing through the interference pattern. The velocity of the particle drop, bubble, or the like is determined using well known laser Doppler anemometry techniques.

39 Claims, 8 Drawing Sheets

| Dimensionless Size $d/d_{max}$ | Dimensionless Signal Amplitude $v/v_{max}$ |
| --- | --- |
| 0.0 | 0 |
| 0.1 | 0.01 |
| 0.2 | 0.04 |
| 0.3 | 0.09 |
| 0.4 | 0.16 |
| 0.5 | 0.25 |
| 0.6 | 0.36 |
| 0.7 | 0.49 |
| 0.8 | 0.64 |
| 0.9 | 0.81 |
| 1.0 | 1.00 |

Signal Voltage Variation With Particle Size

| d/dmax | Phase° | Amplitude (Dimensionless, v/vmax) |
|---|---|---|
| 0 | 0 | 0 |
| 0.1 | 20 | 0.01 |
| 0.2 | 40 | 0.04 |
| 0.3 | 60 | 0.09 |
| 0.4 | 80 | 0.16 |
| 0.5 | 100 | 0.25 |
| 0.6 | 120 | 0.36 |
| 0.7 | 140 | 0.49 |
| 0.8 | 160 | 0.64 |
| 0.9 | 180 | 0.81 |
| 1.0 | 200 | 1.00 |

$$I = I_0 \exp[-2\pi^2/b^2]$$

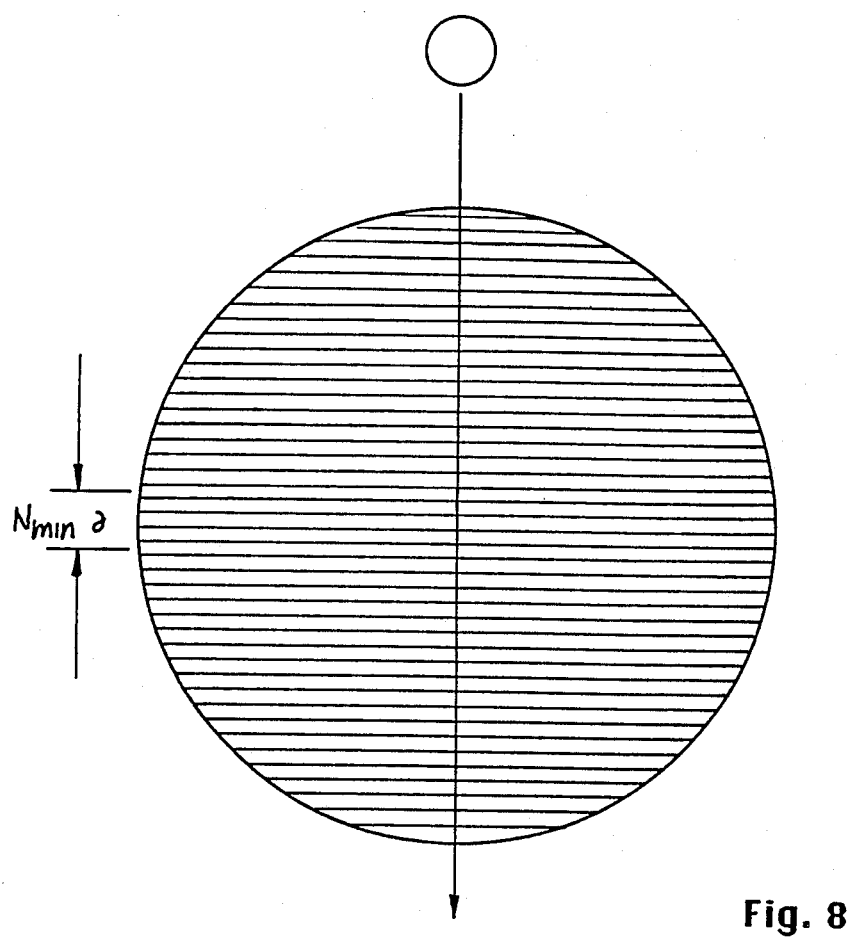
Fig. 8
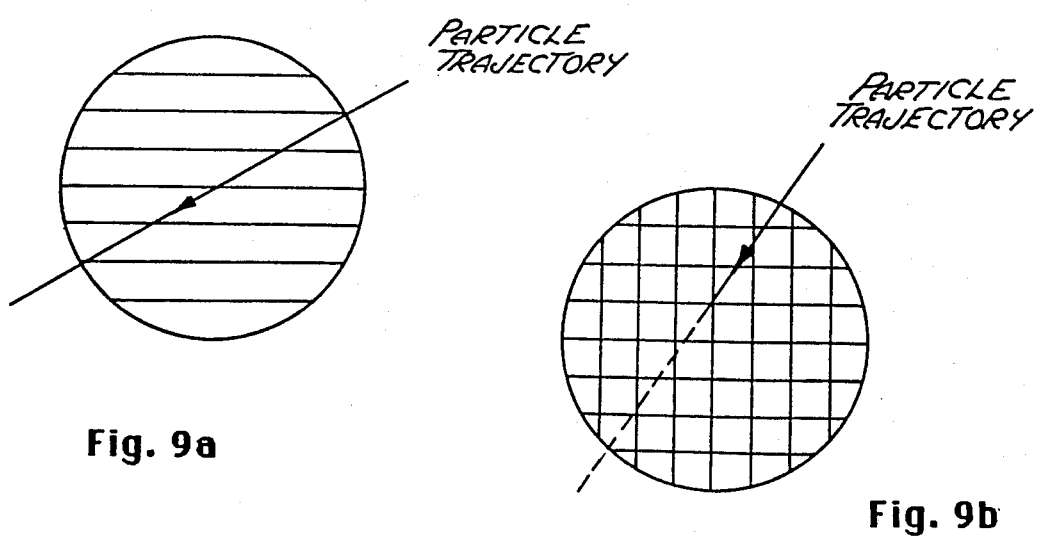
Fig. 9a
Fig. 9b

METHOD FOR MEASURING THE SIZE AND VELOCITY OF SPHERICAL PARTICLES USING THE PHASE AND INTENSITY OF SCATTERED LIGHT

BACKGROUND OF THE INVENTION

1. Related Applications

This application is a continuation in part of U.S. Pat. application Ser. No. 162,053, filed Feb. 29, 1988, entitled "Improved Method for Measuring The Size And Velocity of Spherical Particles Using The Phase And Intensity of Scattered Light", now abandoned.

2. Field of the Invention

The present invention relates to particle size and velocity measurements using scattered laser light detection and, more specifically, relates to such measurements utilizing the Doppler difference frequency, relative signal phase, and intensity of the scattered light.

3. Art Background

There is a need for the detailed measurement of the size and velocity of spherical particles, drops, bubbles, and the like. Areas of application for such measurements include spray nozzle manufacturing, spray combustion research, application of agricultural pesticides and irrigation, aircraft icing studies, atmospheric aerosol research, planetary studies, fuel analysis, and numerous other applications. Several techniques employing laser light scattering have been considered and developed to determine the size and velocity of particles, drops, bubbles, or the like. These techniques include using the intensity of scattered light by particles, particle visibility and the phase/doppler technique for measuring particle size. Each method has had varying degrees of success when applied in real world environments.

Particle size is determinable from the intensity of the light scattered by particles. The higher the intensity of scattered light, the larger the particle size. In one intensity measurement method, the particle size is computed by assuming that a particle scatters light in proportion to the diameter of the particle squared ($d^2$). A more precise method is the well known Lorenz-Mie theory. Using the Lorenz-Mie theory, the light scattering intensity can be predicted for uniformly illuminated spherical particles of arbitrary size. For further information on particle measurements using the intensity technique, see van de Hulst, *Light Scattering By Small Particles* (Dover Publications, 1957). However, particle size measurements which use the intensity of scattered light to determine particle size are quite imprecise because there are a number of unknown parameters such as the incident intensity on the particle, the crosssection of the incident laser light and the particle trajectory through the laser beam. Another method based on light scattering interferometry, referred to as visibility, has been used to measure spherical particles, drops, bubbles, or the like. This method is described by William D. Bachalo, in an article entitled, "Method for Measuring the Size and Velocity of Spheres by Dual-Beam Light-Scatter Interferometry", *Applied Optics*, Vol. 19, Feb. 1, 1980 and in U.S. Pat. No. 4,329,054 which issued on May 11, 1982. The spatial period of the interference fringe pattern generated by a spherical particle, drop, bubble, or the like as it passes through a sample volume defined by the intersection of crossed laser beams is used in determining the particle size and velocity. Several methods have been devised for measuring the spatial period of the fringe pattern. In the above cited references, the fringe pattern was integrated over the receiver lens aperture to obtain the spacing or spatial period of the fringe pattern. The signal visibility which resulted could then be related to the particle size. This method has drawbacks since the dynamic range of the system was limited, and the combined light scattering by the mechanisms of refraction and reflection produced uncertainties in the measurements. Furthermore, other particles passing through the crossed beams produce extinction pulses that tend to distort the signals and hence, compromise the measurement accuracy.

An alternative approach to the visibility method, referred to as the "phase/doppler method", was described by F. Durst and M. Zare in a paper entitled, "Laser Doppler Measurements in Two-Phase Flows", Proceedings of the LDA Symposium, Copenhagen, 1975. The authors provided a basic analysis using a simple geometrical approach to show that the shape and spacing of the fringes formed by the scattered light through reflection and refraction are functions of the angle between the incident laser beams, their wavelength, as well as the direction of light collection and particle diameter. Although the authors claimed that spherical particles could be measured using a double photo-detector apparatus, they later recognized that size measurements required that the distance between the photo-detectors be matched to the expected fringe spacing produced by the scattered light. They concluded that the method was not practical for particle field measurements.

More recently, the method was discussed by, W. D. Bachalo and M. J. Houser in an article entitled "Phase/Doppler Spray Analyzer for Simultaneous Measurements of Drop Size and Velocity Distributions", *Optical Engineering*, Vol. 23, No. 5, 1984. In this article, a more rigorous description of the light scattering theory described by W. D. Bachalo in an earlier article entitled, "Method for Measuring the Size and Velocity of Spheres by Dual-Beam Light Scatter Interferometry", *Applied Optics*, Vol. 19, 1980, was used in the analysis. The theoretical description and experimental verification showed that the method of using signal phase measurements could be used for practical particle field measurements. This was made possible with the selection of appropriate detector separations, on-line observation of the measurements, the use of pairs of detectors, and a single lens system for scattered light detection. The technique was disclosed in U.S. Pat. No. 4,540,283. A similar method was disclosed in U.S. Pat. No. 4,701,051. However, the latter disclosure describes a system using three or more separate receiver lenses and detector systems. The approach disclosed in U.S. Pat. No. 4,701,051 has proved very difficult to operate since each receiver must be carefully aligned to the same measurement point.

Both approaches suffer from the effects of combined light scattering due to reflection and refraction by the particle. This problem was addressed by W. D. Bachalo and M. J. Houser in their report entitled, "Analysis and Testing of a New Method for Drop Size Measurement Using Laser Light Scatter Interferometry", NASA Contract Report No. 174636. The problem was later addressed by Saffman in a report entitled, "The Use of Polarized Light for Optical Particle Sizing", presented at the Third International Symposium on Applications of Laser Anemometry to Fluid Mechanics held in Lisbon, Portugal on July 7–9, 1986. Saffman suggested that a light scatter detection angle of approximately 70° was necessary to avoid errors due to mixed component light scatter detection. This method has the disadvantage of relatively low scattering intensity, lower sensitivity to particle size and inconvenience in applications requiring traversing the sample volume with restricted optical access. Often, backscatter light detection is desirable. Although off-axis backscatter detection has been demonstrated as a viable configuration, errors can occur as a result of the multiple component scattering of reflection and refraction.

The problem is exacerbated when using highly focused laser beams having Gaussian beam intensity distributions. Highly focused beams are required to reduce the sample volume size when coping with high particle number densities. For example, at a light detection angle of 30° with the appropriate polarization, the scattered coefficient for refraction is approximately 80 times that for reflection. However, with a focused beam diameter similar to the sphere diameter and on certain trajectories, the relative incident intensities can be such that the light scattering by reflection and refraction are nearly equal. Because the sign of the phase shift for the fringe pattern produced by reflected light is opposite to that produced by refracted light, the fringes produced by reflection move in the opposite direction.

The present invention discloses a method to overcome this source of error and to provide an alternative means to test the measurements for their accuracy. In addition, the method can provide an alternate means to allow the measurements over several fringes ($N \times 2\pi$) without ambiguity, and without using additional phase measurements which can complicate the signal processing. A method is also described for measuring the sample volume cross section which is known to vary with particle size.

SUMMARY OF THE INVENTION

An improved apparatus and method for determining the change in the effective cross-section of a sample volume defined by two crossed laser beams is disclosed. A laser generation means is provided for generating a pair of coherent laser beams and means are provided to change the separation, intersection angle, and focused diameter of the beams. These beams are directed along an axis, and are caused to cross the axis at a given angle to define an interference pattern constituting a sample volume. A collection apparatus for sensing the light scattered by particles, droplets, bubbles, or the like travelling through the sample volume is provided. In the presently preferred embodiment, the collection apparatus is disposed at preferred off-axis angles including off-axis backscatter with the angle predetermined, and the angle defined by the direction of beam propagation. The collected scattered light is directed onto photodetectors which are coupled to a signal phase determining means, for measuring the relative phase between the signals produced by each photo-detector and a signal amplitude determining means to measure the relative amplitude of the signals produced as the particle, drop, bubble, or the like passes through the sample volume. Sizing means are coupled to the signal phase and amplitude determination means for determining the size of the particle, drop, bubble, or the like from phase and amplitude changes in the received signals.

The present invention determines particle size by the phase of the scattered light signals but overcomes problems associated with this technique, that is, the ambiguity due to the combined light scattering effect by the mechanisms of refraction and reflection. The ambiguity is reduced by examining the amplitude of the scattered light signals to ensure that the amplitudes fall within a certain range of signal amplitudes considered to be reliable. Signals not falling within prescribed maximum and minimum values are rejected from the measurement calculations leaving only those signals which result in meaningful calculations.

BRIEF DESCRIPTION OF THE DRAWINGS

FIG. 8 illustrates a cross-section of the sample volume showing the interference fringe pattern with spacing of $\delta = \lambda/2\sin \gamma/2$.

FIG. 9(a) and 9(b) schematically illustrate orthogonal fringe patterns for measuring sample volume.

DETAILED DESCRIPTION OF THE INVENTION

An apparatus and method for determining the size and velocity of particles, droplets, bubbles, or the like (hereinafter sometimes collectively referred to as "particles") using laser light scattering is disclosed. In the following description for purposes of explanation, numerous details are set forth such as specific wavelengths, angles, frequencies, etc. in order to provide a thorough understanding of the present invention. However, it will be apparent to one skilled in the art that the invention may be practiced without these specific details. In other instances, well known components, structures and electrical processing means have not been described in detail in order not to obscure the present invention unnecessarily.

Figure 1:
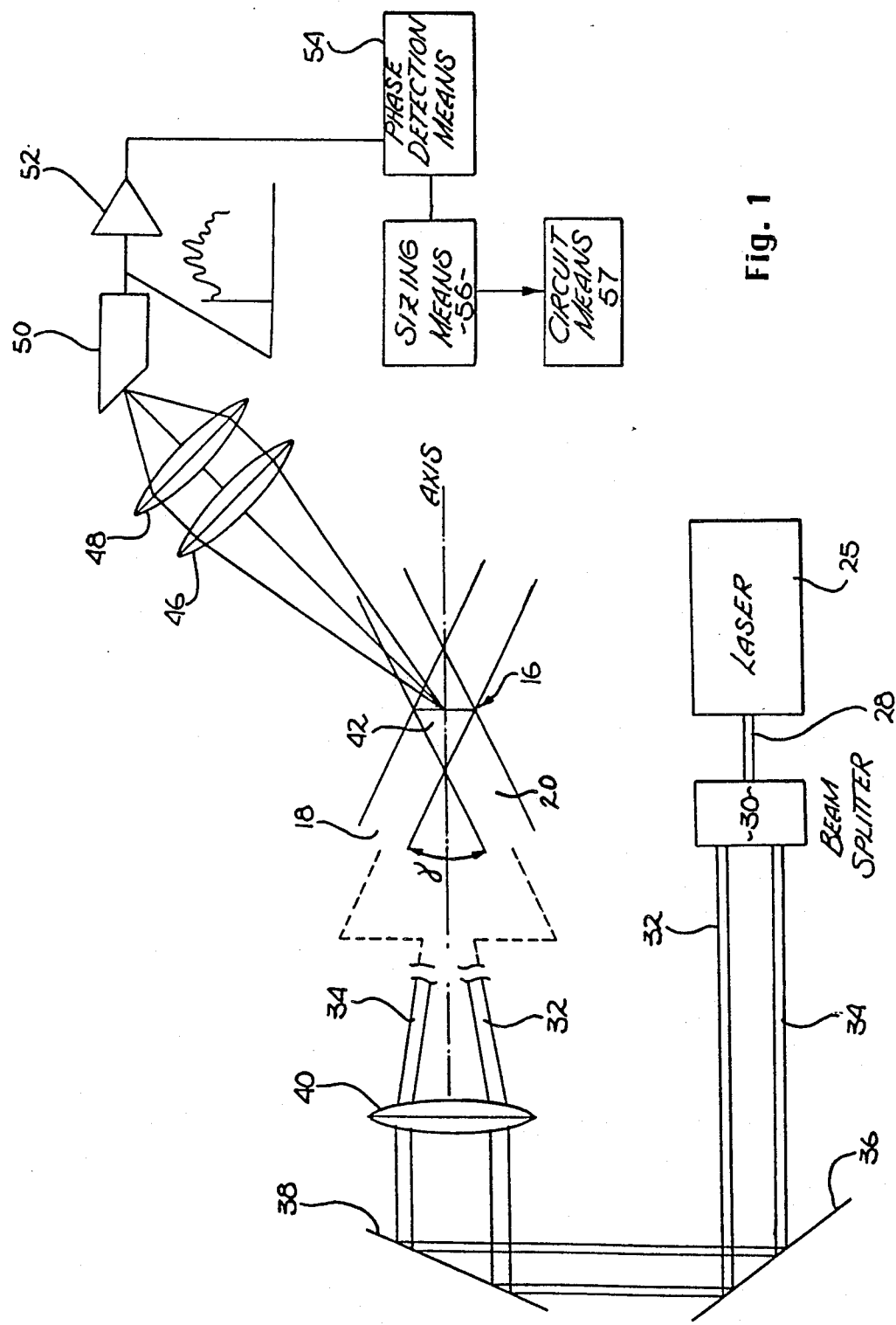
FIG. 1 is a diagrammatical representation of the presently preferred embodiment of the invention.

Referring now to FIG. 1, the apparatus for determining the size and velocity of particles includes a sample volume denoted generally by the numeral 16. The sample volume 16 is defined as the overlap region of a first laser beam 18 and a second laser beam 20 which are caused to cross at an angle gamma with respect to an axis defined through the intersection of the two beams 18 and 20. The laser beams employed by the present invention are generated in the preferred embodiment by a single laser 25. The primary beam 28 generated by laser 25 is passed through a beam splitter 30, thereby forming first and second beams 32 and 34, respectively. Beams 32 and 34 are reflected off of reflectors 36 and 38, and are passed through a focussing lens 40 which causes the beams to cross at the desired angle and form sample volume 16. It should be noted however, that reflectors 36 and 38 are not necessary to practice this invention and an "in-line" system accomplishes the same result.

Note that in FIG. 1, the beams have been broken and then shown in enlarged form in the region of the sample volume. Particles passing through the sample volume 16 scatter light from each beam and the scattered light interferes to form interference fringe patterns in the space surrounding the particle. As previously discussed (see for example, the references to Durst and Zare; and Bachalo), the phase of the scattered light forms the interference fringe pattern at a specific spatial frequency. This spatial frequency is inversely proportional to the particle diameter. The scattered light intensity and hence, the signal amplitude, depends on the particle diameter squared, the incident intensity as well as other parameters that are determined by the optical geometry. The scattered light is sensed by a collection apparatus which includes lenses 46 and 48, which focus the light onto photo-detectors 50. Two or more photodetectors may be used. Photo-detectors 50 are coupled through amplifiers 52 to phase detection means 54 and sizing means 56. A circuit means 57 is coupled to the sizing means 56, to determine the change in the effective cross-section of the sample volume 16 due to size variations of particles, droplets and the like passing through the interference pattern 42, as will be described below.

Figures 2, 3:
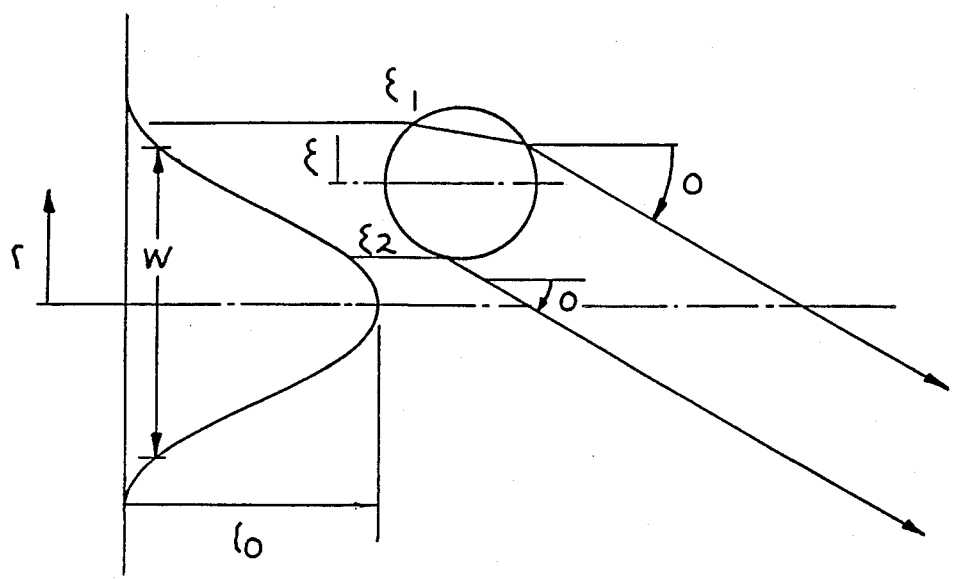
FIG. 2 is a schematic illustrating a Gaussian intensity laser beam incident on a sphere.
FIG. 3 is a table illustrating theoretical amplitude values computed using a geometric technique and their corresponding particle sizes.

FIG. 2 is a schematic illustration of the laser beam with Gaussian intensity incident on a particle or droplet in the shape of a sphere. Phase measurements as described by the inventor, W. Bachalo in U.S. Pat. No. 4,540,283 provide measurements of the particle diameter. However, due to the Gaussian intensity distribution of the laser beam operating in the fundamental mode (TEM∞), and the random particle trajectories through the beam, the combined light scattering by reflection and refraction can produce significant error. This problem occurs, for example, for particles passing on trajectories as illustrated in FIG. 2. At a light scatter detection angle of 30°, light intensity scattered by refraction is approximately 80 times that scattered by reflection. However, on trajectories as shown in FIG. 2, the difference can be much less due to the nonuniform beam intensity with the greater incident intensity falling on the point reflecting light to the detector. When the light scattering by the undesired component (reflection when refraction is expected) is significant, the interference fringe pattern is no longer sinusoidal, but becomes a complex superposition of several spatial frequency components.

The interference fringes produced by reflection also move in the opposite direction to the fringes produced by refraction. This can lead to large measurement errors.

In the present invention, the intensity or signal amplitude information is used as a means of preventing gross errors due to the effect of the aforementioned mixed scattering components that occurs for certain particle trajectories through the beam. More specifically, the amplitude information is used to determine the range of signal values considered reliable enough to result in accurate calculations. If the amplitude measurements falls outside the range of signal values considered to be reliable, the signal measurements (phase and amplitude) are rejected and not utilized in the computation of the particle size.

Preferably the Gaussian beam is first clipped to remove light on the wings of the Gaussian curve at some desired level (e.g., $I/I_o = 1/e^2$). Although it is not necessary to actually clip the Gaussian beam, this approach the advantage of reducing the size of the sample volume 16 and decreasing the number of signals to be processed that will ultimately be rejected. Particles of a given size passing on all trajectories through the beam will produce a range of light scattering intensities of $1/e \leq I/I_{max} \leq 1$.

Preferably the range of reliable signal values is determined empirically by measuring the range of amplitude values (also referred to as intensity values) for a known particle size class. The range of reliable signal values may also be derived from the calculation of the theoretical amplitude range of classes of particle size. A range of acceptable amplitude values is then determined by computing an upper limit above the theoretical value and a lower limit below the theoretical value.

Figure 4:
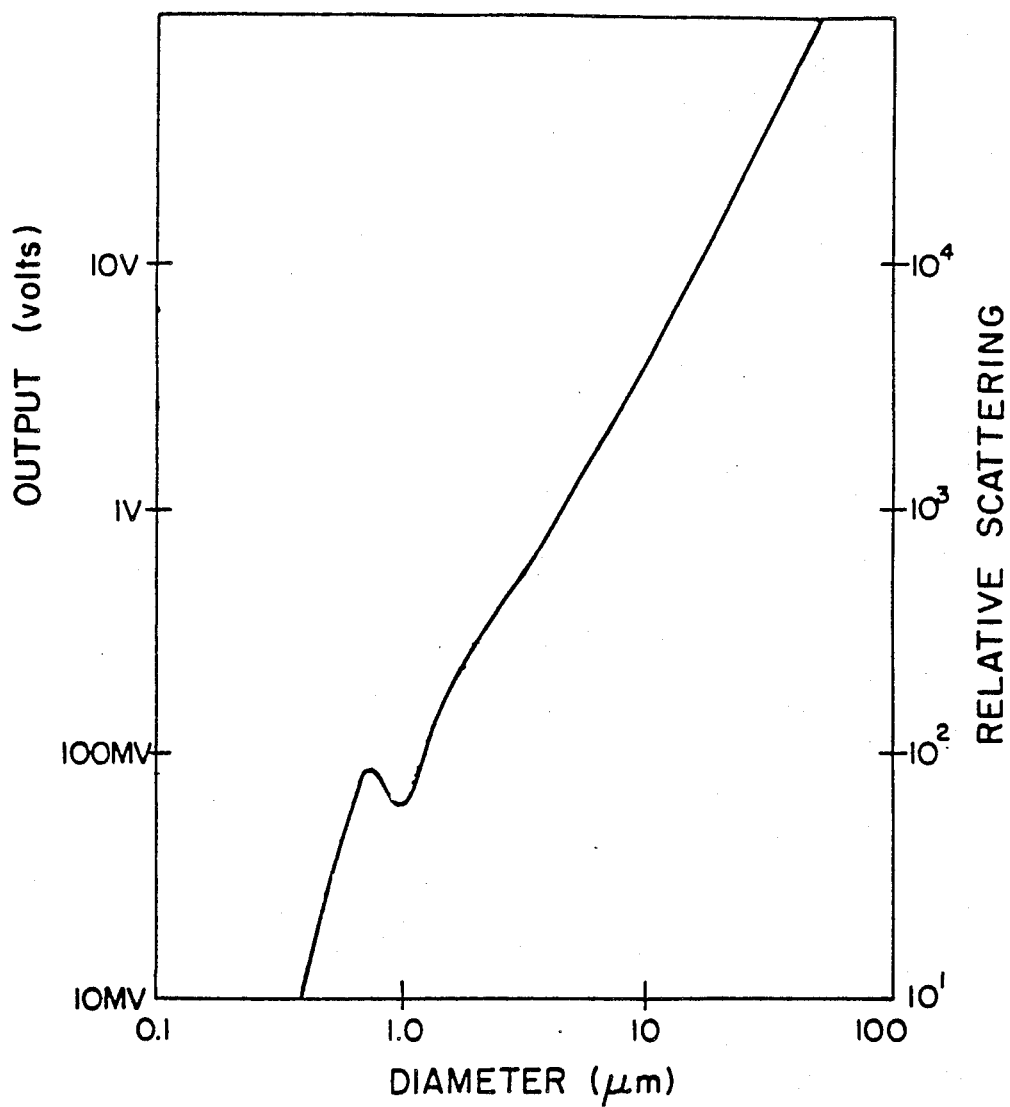
FIG. 4 is a logarithmic graph illustrating the theoretical amplitude values computed for particle size classes using the Lorenz-Mie theory.

The theoretical amplitude values may be determined by assuming that a particle scatters light in proportion to the diameter of the particle squared ($d^2$). An exemplary table containing the theoretical values computed is shown in FIG. 3. Alternatively, the values can be computed using the Lorenz-Mie theory which is computationally intensive but produces accurate results for particle sizes less than 3 microns, where the geometric calculation ($d^2$) breaks down. A logarithmic graph showing the intensity values (volts) for corresponding particle diameters (um) is illustrated in FIG. 4. The theoretical values may be computed as the signal value measurements are taken or may be computed for a range of particle size classes and stored in lookup tables for quick and easy reference.

The upper limit may be the theoretical value computed. Preferably, the upper limit is slightly greater than, for example, 0–.25 volts, the theoretical value to provide a buffering zone. The lower limit on the accepted light scattering intensity may be selected depending upon the requirements for measurement accuracy, the possibility for mixed component light scattering, and other considerations. For example, if as described above, the Gaussian beam is clipped at 1/e, particles of a given size passing on all trajectories through the beam will produce a range of light scattering intensities of $1/e \leq I/I_{max} \leq 1$. Thus, the uncertainty in the particle diameter due to particle trajectory through the clipped Gaussian beam is 1/e to 1 or 0.368 to 1, and the lower limit would preferably be set to approximately ⅓ of the theoretical value.

Figures 5, 11:
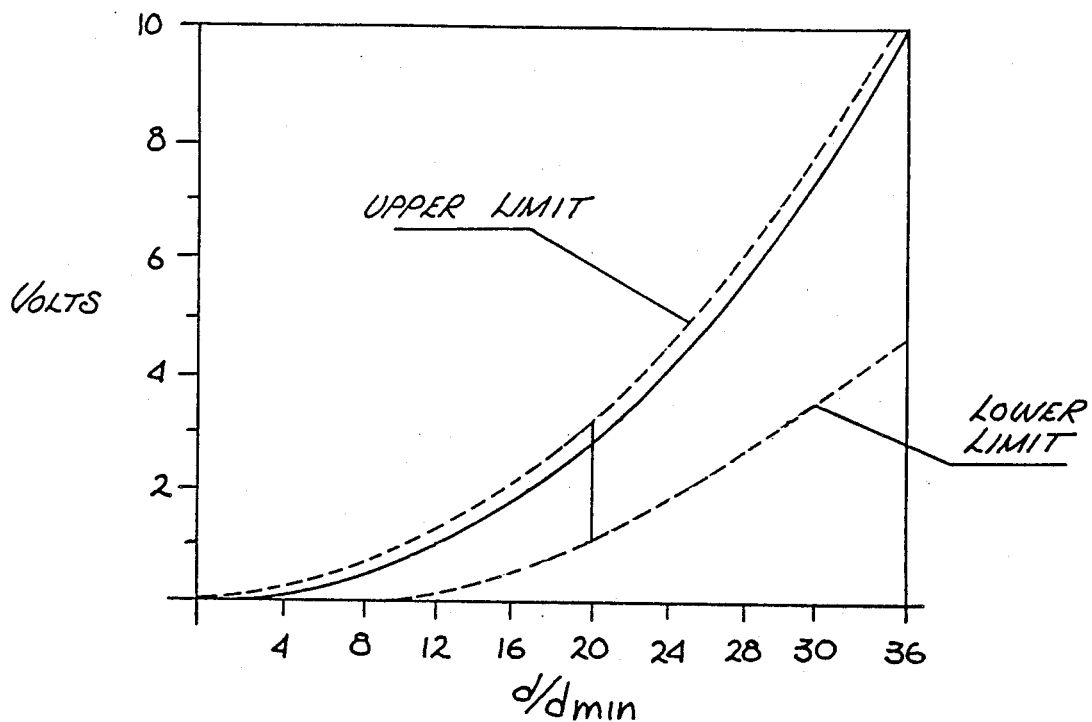
FIG. 5 is a graph of signal voltage variation versus particle size.
FIG. 11 is a table illustrating phase and amplitude values for classes of particle size.

Again assuming that the light scattering intensity is proportional to $d^2$, an example of the diagram of acceptable scattered intensities is shown in FIG. 5. The detector gain is set automatically such that the maximum signal amplitude for each particle size class falls on the $d^2$ curve passing through the maximum allowable signal. The gain is set with the assumption that the phase Doppler method measures the size accurately of most particles passing through the center of the Gaussian beam. This assumption has been shown to be correct by experiment. An acceptable error limit which functions as a buffer, is set on the maximum value shown as the dashed curve marked "upper" on FIG. 5. The dashed curve marked "lower limit" on FIG. 5 can be adjusted to select the range of scattered intensities over which particles will be accepted for each size class. This corresponds to a range of particle trajectories through the Gaussian beam and diameters that will produce signals of acceptable intensities for each size class. The vertical line on the plot is an example of this acceptable band for a specific size (e.g., $d/d_{min}=20$ for this example). The acceptable limits for particle size classes may be computed as the measurements are taken or are preferably computed prior to the measurements and stored in a lookup table for quick reference.

Figure 6:
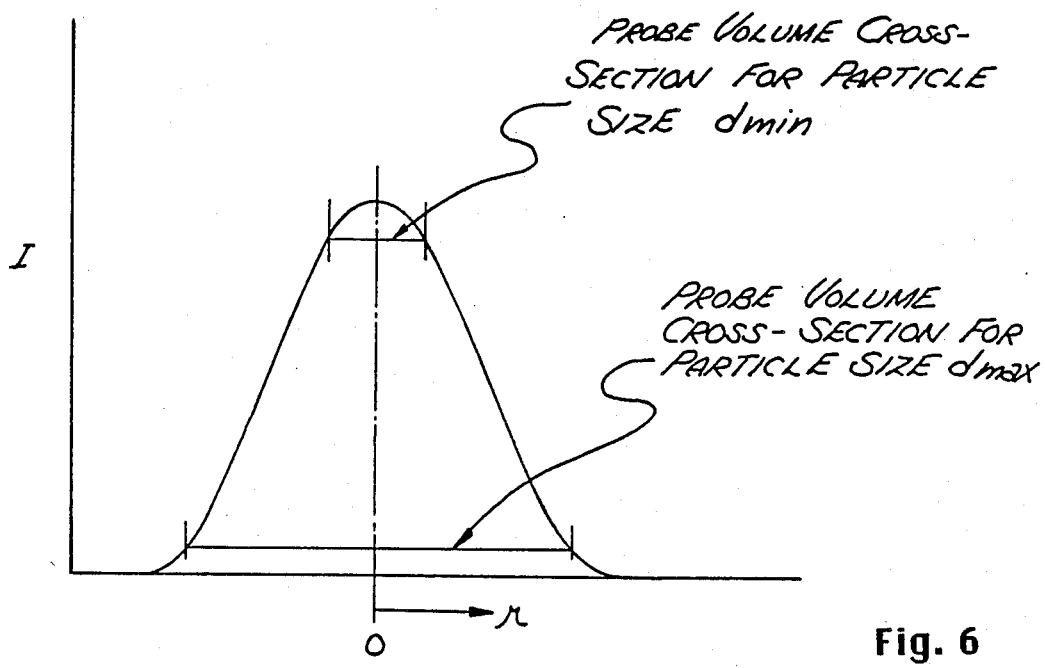
FIG. 6 is a graph of Gaussian laser beam intensity illustrating the variation in sampling cross-section with particle diameter.

The sample volume cross section is known to vary with particle diameter when using Gaussian laser beams [see, D. W. Roberds, Appl. Optics, Vol. 16, pg. 1861, (1977)]. Smaller particles must pass through regions of greater beam intensity (near to the center of the Gaussian) to be detected, whereas larger particles may pass on trajectories further out on the Gaussian intensity profile and still be detected. This results in a bias favoring the measurement of the larger particles (i.e. larger particles are measurable over a larger cross-section and are thus more likely to be measured). This bias and the correcting technique employed are discussed later. FIG. 6 illustrates the variation in sampling cross-section with particle diameter for a Gaussian laser beam. Thus, it can be seen that the sampling cross section increases with particle diameter. The change in sampling volume can be predicted knowing that the beam has a Gaussian intensity distribution and the scattering characteristics of the particles. The equation for the intensity of a Gaussian beam at a certain distance, r, from the center of the beam is given as:

$$I = I_o \exp[-2r^2/b^2]$$

where:
$I_0$ = Maximum intensity of the beam.
r = Radius beam coordinate (distance between particle and center of beam)
b = Radius at which $I/I_0 = 1/e^2$ Assuming that the particles scatter in proportion to their diameter squared (although a more precise value could also be used when appropriate), the resultant expression for the change in sampling cross section, r, with particle diameter, d, is $$r(d) = \left[ r^2(d_{min}) + \frac{b^2}{2} \ln\left\{ (d/d_{min})^2 \cdot \frac{(V+1)}{V_0} \right\} \right]^{\frac{1}{2}}$$

where:
$d_{min}$ = minimum diameter of the distribution of particles measured (smallest particle size to measure) and $V_0$ refer to signal visibility. (See, U.S. Pat. No. 4,329,054, incorporated herein by reference, for determining signal visibility.) This illustrates the bias effect which occurs because a larger particle scatters more light than a smaller particle. It follows that a larger particle can be detected a farther distance away from the center of the beam than where a smaller particle can be detected. Thus it is inherent in this type of measurement that larger particles can be seen more frequently over a larger part of the beam and can be better detected and counted.

Figure 7:
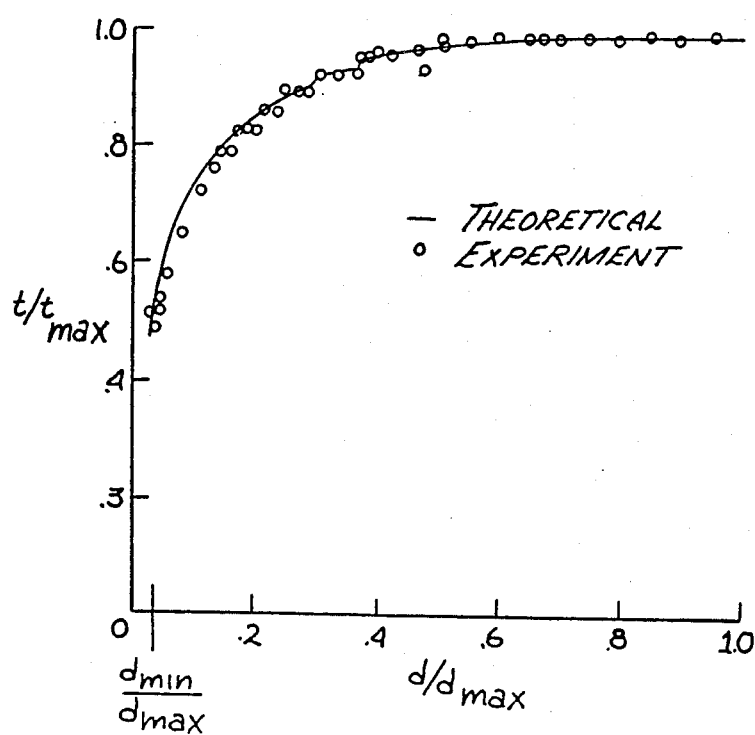
FIG. 7 is a graph illustrating theoretical and experimental results of change in sample volume cross-section versus particle size.

FIG. 7 shows the change in sample volume cross-section with particle size. This approach offers a useful guide to the variation in sampling volume cross section with particle diameter but cannot be relied upon completely due to signal attenuations, beam distortion, etc. in practical flow measurements. Thus, the method of the present invention includes a method to measure the sampling cross section directly and correct the sample volume measurement bias. The experimental data shown in FIG. 7 was obtained using this method.

The sample volume measurement method of the present invention utilizes the implicit fringe pattern formed by the intersecting beams as the measurement scale. FIG. 8 illustrates a cross-section of the sample volume 16 showing the apparent interference fringe pattern with spacing $\delta = \lambda/2\sin(\gamma/2)$. Particles passing on random trajectories through the sample volume 16 will produce signals with the number of cycles corresponding to the number of fringes crossed. However, particles having a certain diameter will travel at different trajectories. Because of this, certain particles may cross more fringes if they travel through the sample volume on a path closer to the center of the laser beams. Thus for a size class, d (i.e., class of particles having diameters within a narrow range), signals produced will reflect varying numbers of fringes crossed. Well known electronics in circuit means 57 counts the number of cycles in each burst signal, or equivalently, circuit means 57 measures the transit time of the beam and this information is used along with the measured particle velocity to determine the beam diameter. For each size class, a statistical distribution of fringe counts is acquired. The maximum number of fringe counts, Nmax, (which is also the most probable value) defines the effective beam diameter, D, and is given as $$D = N_{max} \delta$$

where:
$\delta = \lambda/2 \sin(\gamma/2)$ and $\gamma$ is the beam intersection angle;
$N_{max}$ = maximum number of fringe counts
There is a minimum number of fringe counts, $N_{min}$, required for producing a signal reliable enough to process. Thus, the cross section of sample volume 16, T, is given as $$T = \delta \cdot [N^2_{max} - N^2_{min}]^{\frac{1}{2}}$$

The expression and procedure is used for each particle size class d. Thus the cross section of a sample volume for a size class, T(d), may be written as $$T(d) = \delta[N_{max}(d)^2 - N_{min}^2]^{\frac{1}{2}}$$

where:
$N_{max}(d)$ = maximum number of fringe counts for a size class
$N_{min}$ = minimum number of fringe counts required for reliable signal The measured size distribution is corrected for the nonuniform sampling cross section by first determining the number of particles of a size class measured, or n(d). This value is then multiplied by the ratio of sampling cross-section ($T(d_{max})/T(d)$). That is, $$n(d)_c = n(d) T(d_{max})/T(d)$$

where:

n(d) = number of particles measured in the size class d;

n(d)$_c$ = corrected count for a particle of diameter d;

d$_{max}$ = maximum particle diameter measured in the distribution.

This procedure removes the bias due to nonuniform sampling cross section. The method also serves to define the width of the measurement cross section and with the length along the beam axis defined by the image of the detector aperture, the sampling cross-sectional area is defined. Accurate definition of the sample volume cross-sectional area is required for measurements of particle number density and volume flux. The method assumes that the mean particle angle of trajectory is orthogonal to the interference fringe pattern or correspondingly, in the plane of the intersecting beams. If this is not true, two components of the velocity can be measured to determine the angle of trajectory for each particle size class. FIGS. 9(a) and 9(b) illustrate a schematic of orthogonal fringe patterns for measuring the sample volume. The relative fringe counts or corrected fringe counts for a size class, N(d)$_c$, are therefore adjusted as follows:

$$N(d)_c = N(d)/\cos\theta(d)$$

where:

$\theta(d)$ = mean angle of trajectory for particles of diameter, d;

N(d) = number of fringe counts for a size class

The cycle counts from both components may be used separately as $$N_R(d) = [N_x^2(d) + N_y^2(d)]^{\frac{1}{2}}$$

where:

$N_R(d)$ = number of resultant fringe counts for a size class $N_X(d)$ = number of x-component fringe counts for a size class $N_Y(d)$ = number of y-component fringe counts for a size class Although the above procedure may be used directly, the number of samples at the extremes of the size distribution, and particularly of the largest particle may be small providing inadequate sampling statistics for proper definition of the sampling cross section. Thus, the knowledge that the variation of the sampling volume follows a natural log curve is used to fit a curve to the measured results. The best fit curve is then used with proper weighting for the number of samples in each size class to produce the sample volume variation for correcting the size distribution. This method tends to smooth some of the variations that can occur in the measurements due to having too few samples in the distribution for each size class. When the intensity or signal amplitude is used to validate the measurements obtained from the phase method, the curve fitting procedure must be modified to allow for the lower limit of signal amplitude accepted which will manifest as a lower limit on the sample volume width. This effect can be predicted easily using the selected lower cut-off value of the signal amplitude.

Figure 10:
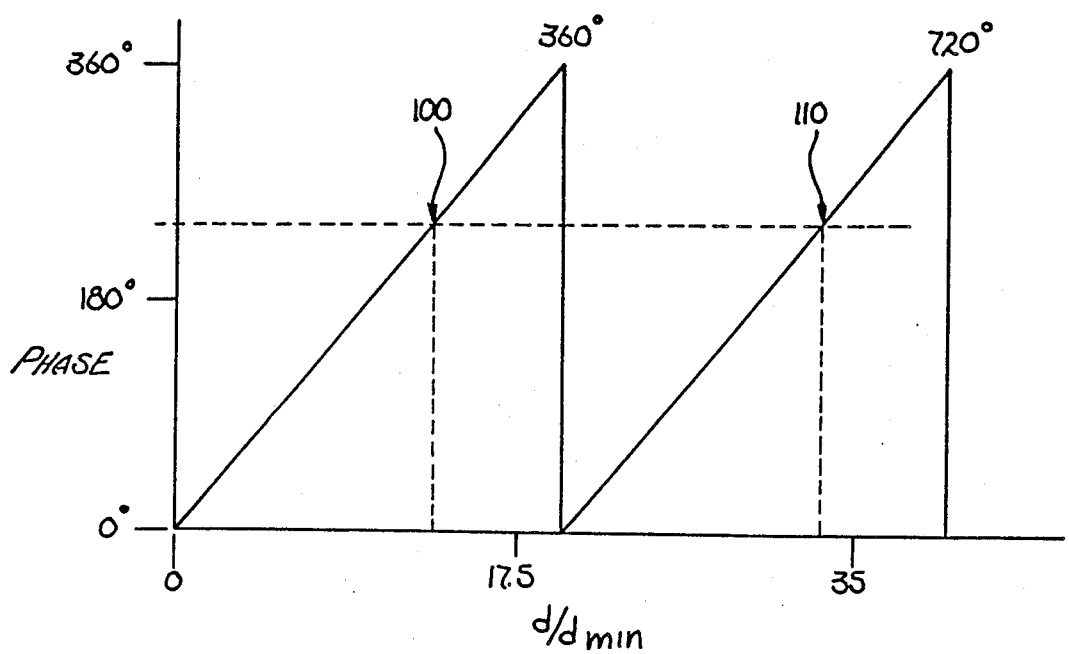
FIG. 10 schematically illustrates the phase for particle sizing over multiple fringe cycles.

The signal amplitude information may also be used to allow measurements of phase shifts that exceed $2\pi(360°)$ using only one pair of detectors or in conjunction with the method using multiple pairs of detectors. The limitation on the number of cycles of signal phase difference over which the method can be used depends on the range of the incident intensities accepted. That is, since the laser beam has a Gaussian beam intensity distribution, the incident intensity will vary based upon the particle trajectory. However, the beam intensity distribution can be clipped to limit the range of signal amplitudes for each particle size class. FIG. 10 shows the phase diagram for a range of particle sizes over more than one phase difference cycle. In the example of FIG. 10, the phase is shown as varying over two cycles($4\pi$ or 720°). Clearly two particle sizes will correspond to each phase measurement since the measured phase repeats after $2\pi$. Whether the particle measured produces a phase shift $\phi$ within the first cycle or $360° + \phi$ corresponding to the second cycle can be established from the signal amplitude information. Since the signal amplitude varies approximately as the particle diameter squared (see, for example, FIG. 11), the difference in signal amplitude is greater than the signal amplitude variation due to the trajectory through the beam. In the worst case where the full phase range of $4\pi(720°)$ is used for the permitted size range of 35:1 (limited by signal amplitude considerations) a signal amplitude range of 4 to 1 results. That is, the dimensionless signal amplitude for a particle producing a 360° phase shift would be approximately 0.25 whereas the dimensionless signal amplitude for a particle producing a phase shift of 720° would be 1.0. Thus, the signal amplitudes can be used to reliably identify the cycle of the phase measurement ($\phi$ or $\phi + 360$) and, hence, the size of the particle. The phase information and corresponding amplitude information may be computed for each measurement or, alternatively, may be calculated ahead of time and incorporated into a lookup table for easy reference.

As illustrated in FIG. 10, the particle size at location 100 equals 15 microns, with a signal amplitude defined as $$15^2/35^2 \times 10 = 1.84 V.$$

At location 110, the particle size equals 30 microns, with a signal amplitude defined as $$30^2/35^2 \times 10 = 7.35 V.$$

Figure 12:
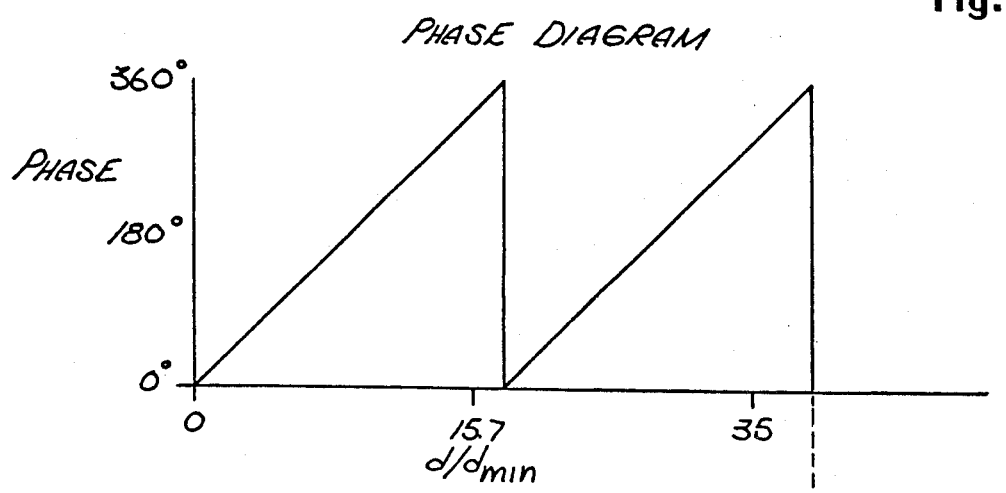
FIG. 12 is a graph of phase and corresponding size distribution when particle size exceeds selected range.
Figure 13:
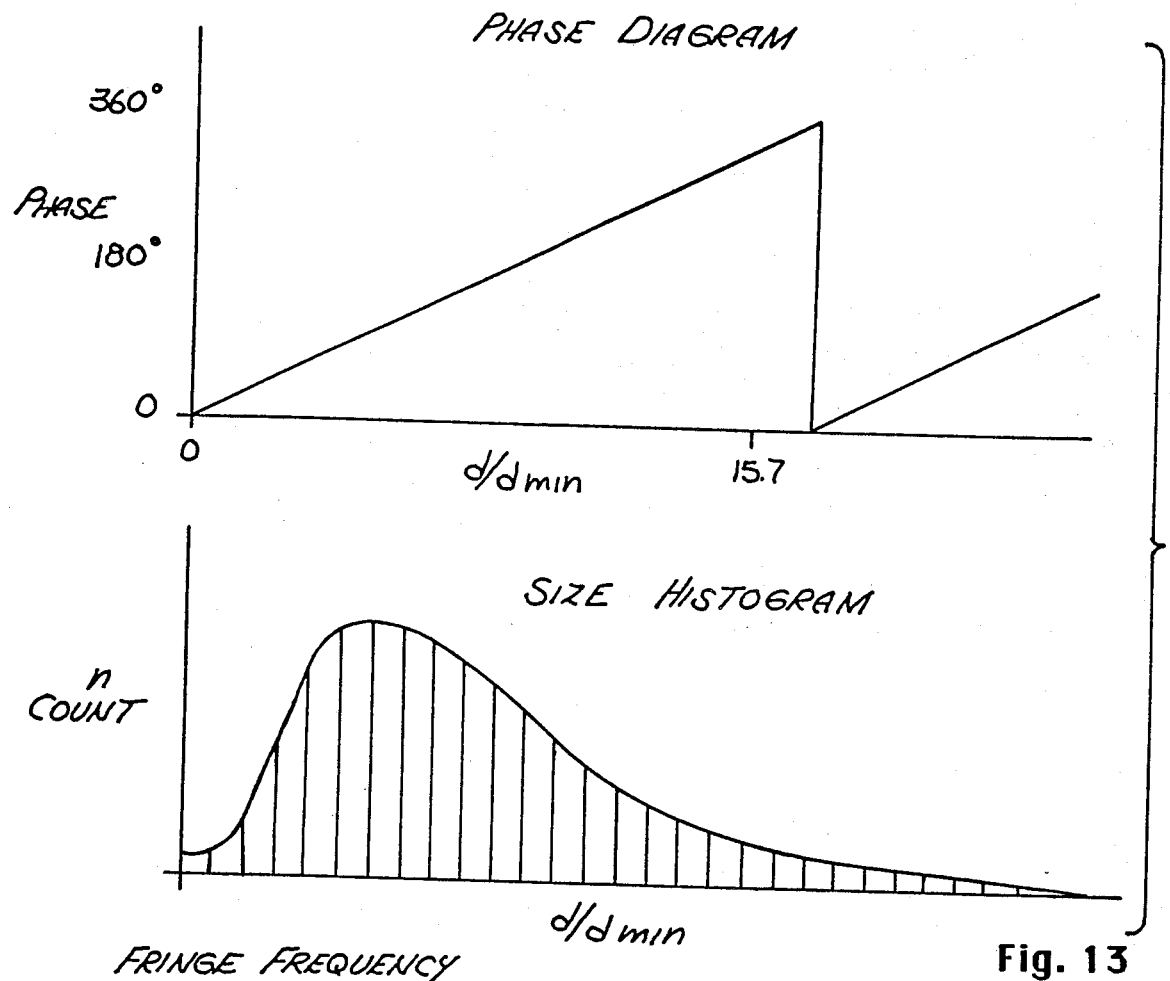
FIG. 13 is a graph of phase and corresponding size distribution after size range adjustment.

Software has been generated to limit the size range displayed to 2 cycles or 720° of phase shift. If larger particles are present that produce a phase shift of greater than $4\pi$, the real time display will show the size distribution exceeding the upper limit (see FIG. 12). Since size distributions are continuous, this will be apparent to those in the field using the method. At this point, the sizing parameters are changed to bring the distribution within the measurement bounds. FIG. 13 illustrates the phase diagram and corresponding size distribution after adjusting the size range selection to accommodate the actual size distribution.

Figure 14:
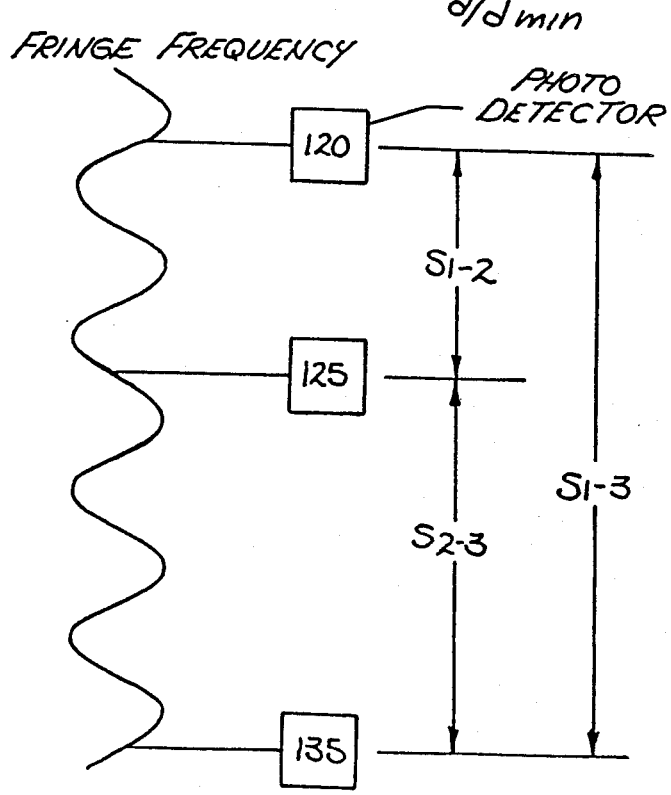
FIG. 14 schematically illustrates the use of redundant phase measurements to measure greater than 360° of phase shift at high sensitivity.

Referring now to FIG. 14, in the presently preferred embodiment, photo-detectors 52 comprise at least two photo-detector's 120 and 125. When using 2 or more pairs of detectors, the phase measurements can be extended over several cycles of phase ($n \times 2\pi$) where n is the number of cycles. However, the pair of detectors spaced close together will limit the upper size of the particle that can be measured without ambiguity. That is, the fringe spacing can be less than the closest spaced detectors (detectors 120 and 125 on FIG. 14). Proper selection of the detector spacings can be used to perform measurements with the phase varying more than 360° on each detector pair. By measuring the phase shift between detectors 120 and 125, and between 120 and 135, for each particle, the measurements can be compared to evaluate over which cycle each measurement occurred. The redundant measurements can then be further compared to estimate the reliability of each measurement. These measurements with progressively increased size range sensitivity, selected by increased detector spacings, serve to maximize the size sensitivity over each particle size measurement.

Reliable measurements in the neighborhood of 360° have been achieved using the method and apparatus of the present invention. At these values, a slight measurement error over the signal will result in a variation between 360° and 0° corresponding to the next cycle. Phase shifting circuitry has been incorporated to eliminate the potential for relatively large measurement error. The value of the measured phase of the lower sensitivity range could be used when the high sensitivity range is near 360°. However, this will lead to discontinuities in the size range sensitivity. The signal phase shifting method and range selection logic have been incorporated in the present invention and eliminate this error source.

Thus the present invention includes a phase shifting method which splits the signals from the detectors and shifts the phase of one of the signals from each pair by 180°. Circuitry is then used to determine when the signal phase differences approach 360°. This can be recognized from the fact that the difference between the corresponding signals on the other pair will be near 180° which can be done accurately. The potentially large errors produced by attempting the measurement near 360° are avoided.

Thus, an improved system and method for determining the size and velocity of particles, droplets and the like, has been disclosed. Although the present invention has been described with reference to FIGS. 1-14, it will be understood that the Figures are for illustration only and should not be taken as limitations on the invention.

I claim:

1. In an apparatus for measuring parameters associated with particles, droplets and the like employing first and second Gaussian laser beams caused to cross to establish an interference pattern forming a sample volume, a method for detecting errors due to mixed components in light scattered by said particles, droplets and the like passing through said interference pattern, comprising the steps of:
    (a) generating said first and second Gaussian laser beams and directing said beams to cross at a known angle to form said sample volume;
    (b) collecting said light scattered by said particles, droplets and the like passing through said sample volume and determining the phase of said scattered light;
    (c) determining the size of said particles, droplets and the like from the phase of said scattered light;
    (d) determining the amplitude of said scattered light and comparing said amplitude to predefined upper and lower amplitude limits for the particle size, such that if said amplitude determined is outside said limits an error is detected and said measurement is considered invalid.

2. The method as defined by claim 1, wherein said amplitude is further compared to phase angle values stored in a look-up table, said table providing a corresponding phase angle for an inputted amplitude and determines if said amplitude corresponds to a phase angle greater than $2\pi$.

3. The method as defined by claim 1, wherein said upper and lower amplitude limits are stored in a look-up table for each size class of said particles, droplets and the like.

4. The method as defined by claim 1, wherein said upper limit is determined by computing a theoretical value for the size class of the particle size determined and increasing the theoretical value by predetermined amount indicative of a buffer zone.

5. The method as defined by claim 4, wherein the theoretical value is computed using the Lorenz-Mie theory.

6. The method as defined by claim 4, wherein the theoretical value is computed using a geometric technique which assumes that the signal amplitude is equal to the particle diameter squared.

7. The method as defined by claim 4 wherein the predetermined amount is in the range of 0-0.25 volts.

8. The method as defined by claim 1, wherein said lower limit is determined by computing a theoretical value for the size class of the particle size determined and decreasing the theoretical value by a predetermined amount.

9. The method as defined by claim 8, wherein the theoretical value is computed using the Lorenz-Mie theory.

10. The method as defined by claim 8, wherein the theoretical value is computed using a geometric technique which assumes that the signal amplitude is equal to the particle diameter squared.

11. The method as defined by claim 8 wherein the predetermined amount is approximately one-third of the theoretical value.

12. The method as defined by claim 1, wherein said collecting step includes sensing said scattered light using two or more spaced apart photodetectors.

13. The method as defined by claim 1, wherein said mixed components comprise light reflected off of and refracted through said particles, droplets and the like.

14. In a system for measuring parameters associated with particles, droplets and the like employing laser light scattering, an apparatus for detecting errors due to mixed components in said scattering, comprising:
    laser generation means for generating first and second Guassian laser beams and directing said beams to cross forming a sample volume;
    collection means for collecting the scattered light due to said particles, droplets and the like passing through said sample volume, and converting said scattered light into electrical signals;
    phase detection means coupled to said collection means for determining the phase and amplitude of said signals;
    sizing means coupled to said phase detection means for determining the size of said particle, droplet and the like from the phase of said signals, said sizing means further comparing said amplitude to predefined upper and lower amplitude limits for the particle size, such that if said amplitude is outside said limits an error is detected and said measurement is considered invalid.

15. The apparatus as defined by claim 14, wherein said sizing means further compares said amplitude to phase angle values stored in look-up table means coupled to said sizing means, said look-up table means providing a corresponding phase angle for an inputted amplitude, and determines if said amplitude corresponds to a phase angle greater than $2\pi$.

16. The apparatus as defined by claim 14, wherein said upper and lower amplitude limits are stored in a look-up table for each class size of said particles, droplets and the like.

17. The apparatus as defined by claim 14, wherein said upper limit is determined by computing a theoretical value for the size class of the particle size determined and increasing the theoretical value by a predetermined amount indicative of a buffer zone.

18. The apparatus as defined by claim 17, wherein the theoretical value is computed using the Lorenz-Mie theory.

19. The apparatus as defined by claim 17, wherein the theoretical value is computed using a geometric technique which assumes that the signal amplitude is equal to the particle diameter squared.

20. The apparatus as defined by claim 17 wherein the predetermined amount is in the range of 0-0.25 volts.

21. The apparatus as defined by claim 14, wherein said lower limit is determined by computing a theoretical value for the size class of the particle size determined and decreasing the theoretical value by a predetermined amount.

22. The apparatus as defined by claim 21, wherein the theoretical value is computed using the Lorenz-Mie theory.

23. The apparatus as defined by claim 21, wherein the theoretical value is computed using a geometric technique which assumes that the signal amplitude is equal to the particle diameter squared.

24. The apparatus as defined by claim 21 wherein the predetermined amount is approximately one-third of the theoretical value.

25. The apparatus as defined by claim 14, wherein said collecting means senses said scattered light using two or more spaced apart photodetectors.

26. In an apparatus for measuring or sensing parameters associated with particles, droplets and the like employing first and second Gaussian laser beams caused to cross to establish an interference pattern forming a sample volume, a method for determining the change in the effective cross-section of said sample volume, comprising the steps of:
(a) generating said first and second Gaussian laser beams and directing said beams to cross at a known angle, said interference pattern having an apparent spacing defined as $\delta$;
(b) collecting the scattered signal created by said particles, droplets and the like passing through said sample volume;
(c) determining the maximum ($N_{max}$) and minimum ($N_{min}$) number of interference fringes crossed by said particles, droplets and the like, of a class of particles having the same diameter passing through said sample volume wherein $N_{min}$ is the number of fringes detected to produce a signal reliable enough for later use;
(d) determining the change in the effective cross-section of said sample volume due to size variations of said particles, droplets and the like passing through said interference pattern, said change in said cross-section being defined as:

$$T(d) = \delta[N_{max}(d)^2 - N_{min}(d)^2]^{\frac{1}{2}}$$

where:
T=sample volume cross-section
d=diameter of said particle, droplet and the like
whereby the effective apparent cross-section of said sample volume is determined for a class of said particles, droplets and the like having a diameter d.

27. The method as defined by claim 26, wherein $$\delta = \lambda/2\sin(\gamma/2)$$

where:
$\lambda$=the wavelength of said first and second laser beams;
$\gamma$=the known angle of the beam intersection.

28. The method as defined by claim 26, further including the steps of:
determining the number of particles in a size class measured; and correcting the particle size distribution to account for the said change of cross section of said sample volume due to a non-uniform sampling of said cross-section such that:

$$n(d)_c = n(d)T(d_{max})/T(d)$$

where:
n(d)=number of particles measured in the size class d;
$n(d)_c$=corrected count for a particle, droplet and the like having diameter d;
$d_{max}$=maximum diameter of said particle, droplet and the like measured in the size distribution.

29. The method as defined by claim 28, wherein said apparatus includes collection means for collecting said scattered signal.

30. The method as defined by claim 29, wherein said collection means includes at least two photo-detectors spaced apart from one another such that said spacing of the finges formed by the scattered light is less than the distance between said first and second photo-detectors.

31. The method as defined by claim 30, wherein said collection means includes a third photo-detector spaced apart from said first and second photo-detector.

32. The method as defined by claim 31, further including the step of determining the phase shift of said scattered signal between said first and second photo-detectors and said first and third photo-detectors to determine the size range over which said particle, droplet and the like is measured.

33. In a system for measuring or sensing parameters associated with particles, droplets and the like employing laser scattering, an apparatus for determining the change in the effective cross-section of two crossed laser beams forming a sample volume, comprising:
laser generation means for generating first and second Gaussian laser beams and directing said beams to cross at a known angle ($\gamma$), said crossed beams forming an interference pattern defining said sample volume, said interference pattern having an apparent spacing ($\delta$);
collection means for collecting the scattered signal created by said particle, droplet and the like passing through said sample volume;
circuit means coupled to said collection means for determining the maximum ($N_{max}$) and minimum ($N_{min}$) number of interference fringes crossed by said particles, droplets and the like, of a class of particles having the same diameter passing through said sample volume;

said circuit means further determining the change in the effective cross-section of said sample volume due to size variations of said particles, droplets and the like passing through said interference pattern, said change in said cross section being defined as:

$$T(d) = \delta[N_{max}(d)^2 - N_{min}(d)^2]^{\frac{1}{2}}$$

where:
T = sample volume cross-section;
d = diameter of said particle, droplet and the like; whereby the effective apparent cross-section of said sample volume is determined for a class of said particles, droplets and the like having a diameter d.

34. The apparatus as defined by claim 33, wherein $$\delta = \lambda/2\sin(\gamma/2)$$

where:
λ = the wavelength of said first and second laser beams;
γ = the known angle of the beam intersection.

35. The apparatus as defined by claim 34, wherein said circuit means utilize the number of particles in a size class measure and includes correction means for correcting said change of cross-section of said sample volume due to a non-uniform sampling of said cross-section, such that:

$$n(d)_c = n(d)T(d_{max})/T(d)$$

where:
n(d) = number of particles measured in the size class d;
$n(d)_c$ = corrected count for a particle, droplet and the like having diameter d;
$d_{max}$ = maximum diameter of said particle, droplet and the like measured in the size distribution.

36. The apparatus as defined by claim 35, wherein said collection means includes at least two photo-detectors spaced apart from one another such that the fringe spacing produced by the scattered light signal in the plane of the detectors is less than the distance between said first and second photodetectors.

37. The apparatus as defined by claim 36, wherein said collection means includes a third photo-detector spaced apart from said first and second photo-detector.

38. The apparatus as defined by claim 37, wherein said circuit means determines a first phase shift of said scattered signal between said first and second photodetectors and a second phase shift of said first and third photo-detectors to determine the size range over which said particle, droplet and the like is measured.

39. The apparatus as defined by claim 38, wherein said circuit means further comprises:
means for determining that the signals collected by two photodetectors are approximately 360 degrees out of phase;
a phase shifting means to shift the phase of one of the signals collected by one of the photodetectors 180 degrees such that errors due to ambiguity of overlapping signals is minimized.

* * * * *

UNITED STATES PATENT AND TRADEMARK OFFICE
CERTIFICATE OF CORRECTION

PATENT NO. : 4,986,659
DATED : January 22, 1991
INVENTOR(S) : William D. Bachalo It is certified that error appears in the above-indentified patent and that said Letters Patent is hereby corrected as shown below:

Column 8, Line 39;    Delete "$D=N7ax^{\delta}$";    Insert in place thereof --

$D = N_{max}\delta$ --

Signed and Sealed this

Tenth Day of October, 1995

Attest:

BRUCE LEHMAN

*Attesting Officer*    Commissioner of Patents and Trademarks